(12) United States Patent
Winterfeld et al.

(10) Patent No.: US 6,284,907 B1
(45) Date of Patent: Sep. 4, 2001

(54) PROCESS FOR THE PREPARATION OF 1,3-DIHALO-1,1,3,3-TETRA(ORGANYL) DISILOXANES

(75) Inventors: Jörn Winterfeld; Bors C. Abele, both of Burghausen (DE)

(73) Assignee: Wacker-Chemie GmbH, München (DE)

( * ) Notice: Subject to any disclaimer, the term of this patent is extended or adjusted under 35 U.S.C. 154(b) by 0 days.

(21) Appl. No.: 09/718,714

(22) Filed: Nov. 22, 2000

(30) Foreign Application Priority Data

Dec. 23, 1999 (DE) .............................................. 199 62 563

(51) Int. Cl.$^7$ ...................................................... C07F 7/08
(52) U.S. Cl. ............................................................ 556/452
(58) Field of Search ............................................... 556/452

(56) References Cited

U.S. PATENT DOCUMENTS

| | | | | |
|---|---|---|---|---|
| 3,646,090 | * | 2/1972 | Bennett ................................ | 556/452 |
| 3,687,642 | * | 8/1972 | Koerner et al. ...................... | 556/452 |
| 5,247,045 | * | 9/1993 | Durfee et al. ....................... | 556/452 X |
| 5,258,535 | | 11/1993 | Ishikawa et al. . | |
| 5,473,037 | * | 12/1995 | Itoh et al. ........................... | 556/452 X |
| 5,476,916 | * | 12/1995 | Pachaly et al. ...................... | 556/452 X |

FOREIGN PATENT DOCUMENTS

| | | |
|---|---|---|
| 35 18 605 A1 | 11/1986 | (DE) . |
| 0 557 762 A1 | 9/1993 | (EP) . |
| 58 4792 | 1/1983 | (JP) . |
| 2 145591 | 6/1990 | (JP) . |

OTHER PUBLICATIONS

International Search Report—Mailed Mar. 23, 2001.
English Derwent Abstract Corresponding To DE 35 18 605 AN 1986–319922 [49], 1986.
English Derwent Abstract Corresponding To JP 58 4792 AN 1983–16562K [07], 1983.
English Derwent Abstract Corresponding To JP 2145591 AN 1990–21445 [81], 1990.
R. Chawla et al., Synthetic Communications, 29 (1999), pp. 3499–3501.
H.X. Zhang et al., Synthetic Communications, 17 (1997), pp. 1299–1307.

* cited by examiner

*Primary Examiner*—Paul F. Shaver
(74) *Attorney, Agent, or Firm*—Brooks & Kushman P.C.

(57) ABSTRACT

1,3-dihalo-1,1,3,3-tetra(organyl)disiloxanes of the general formula $$XR_2Si-O-SiR_2X \qquad (1)$$

are prepared by reacting hydrogen halide with the corresponding 1,3-dihydro-1,1,3,3-tetra(organyl)disiloxanes of the general formula $$HR_2Si-O-SiR_2H \qquad (2),$$

in which R is an alkyl or halogen substituted alkyl group and X is halogen, in the presence of a catalyst selected from transition metals of the 8th subgroup of the periodic table of the elements, or compounds or complexes of these transition metals.

20 Claims, No Drawings

PROCESS FOR THE PREPARATION OF 1,3-DIHALO-1,1,3,3-TETRA(ORGANYL) DISILOXANES

TECHNICAL FIELD

The invention relates to a process for the preparation of 1,3-dihalo-1,1,3,3-tetra(organyl)disiloxanes.

BACKGROUND ART 1,3-dihalo-1,1,3,3-tetra(organyl)disiloxanes are used not only in the preparation of specific polysiloxanes but increasingly as protective group reagents in organic synthesis. Probably the most thoroughly investigated and most widely used disiloxanes of this class of substances are 1,3-dichloro-1,1,3,3-tetramethyldisiloxane and 1,3-dichloro-1,1,3,3-tetraisopropyldisiloxane.

These compounds can be prepared in principle by chlorinating 1,3-dihydro-1,1,3,3-tetra(organyl)disiloxanes. However, the chlorination processes described in the literature are generally unsuitable for scaling up to industrial production and also frequently have further disadvantages.

Thus, although the chlorination is possible in principle using elemental chlorine in the presence of a catalyst, for example according to JP-A-02145591, the substitution often takes place not only selectively at the desired silicon-bonded hydrogen but also at the organyl radicals. Purification of the desired molecule is often difficult and expensive.

The chlorination of 1,3-dihydro-1,1,3,3-tetramethyldisiloxane with copper(II) chloride in the presence of copper(I) iodide is described in EP-A-557 762 or the corresponding U.S. Pat. No. 5,258,535. Substantial disadvantages of this process are that at least one (mole) equivalent of copper(II) chloride is required per H—Cl exchange, and that considerable amounts of copper salts have to be handled, especially on an industrial scale. In addition, a solvent is required for the reaction.

Use of allyl chlorides is disclosed in DE-A-351 8605, of chlorohydrocarbons in JP-A-58004792, of acid chlorides in H. X. Zang et al., Synth. Commun. 17 (1987) 1299–1307, and of hypochlorites in R. Chawla et al., Synth. Commun. 29 (1999) 3499–3501, all generally in the presence of a specific catalyst for the chlorination of 1,3-dihydro-1,1,3,3-tetra (organyl)disiloxanes. Owing to the toxicological properties of these chlorinating agents, however, industrial use is problematic. Moreover, byproducts which have to be separated from the desired product by distillation are generated in these chlorination reactions.

DISCLOSURE OF INVENTION

The object of the invention is to provide a simple and in particular economical process for the preparation of 1,3-dihalo-1,1,3,3-tetra(organyl)disiloxanes in the presence of a catalyst selected from transition metals of the 8th subgroup of the periodic table of the elements, compounds of transition metals of the 8th subgroup, and complexes of transition metals of the 8th subgroup.

DETAILED DESCRIPTION OF THE INVENTION

The invention relates to a process for the preparation of 1,3-dihalo-1,1,3,3-tetra(organyl)disiloxanes of the general formula $$XR_2Si\text{—}O\text{—}SiR_2X \quad (1)$$

by reacting hydrogen halide with 1,3-dihydro-1,1,3,3-tetra (organyl)disiloxanes of the general formula $$HR_2Si\text{—}O\text{—}SiR_2H \quad (2),$$

in which

R are identical or different and denote $C_{1\text{-}20}$ hydrocarbon radicals optionally substituted by fluorine or chlorine atoms, and X are identical or different and denote a halogen atom, in the presence of a catalyst selected from transition metals of the 8th subgroup of the periodic table of the elements, compounds of transition metals of the 8th subgroup and complexes of transition metals of the 8th subgroup.

Examples of hydrocarbon radicals R are alkyl radicals such as the methyl, ethyl, n-propyl, isopropyl, n-butyl, sec-butyl, tert-butyl, thexyl, n-hexyl, n-heptyl, n-octyl, and octadecyl radicals; cycloalkyl radicals such as the cyclopentyl, cyclohexyl, and methylcyclohexyl radicals; and aralkyl radicals, such as the benzyl, phenylethyl, phenylnonyl, 2-phenylpropyl, and fluorenyl radicals.

Examples of substituted hydrocarbon radicals R are the 3,3,3-trifluoropropyl, the 3,3,4,4,5,5,6,6,6-nonafluorohexyl and the 2,3,4,5,6-pentafluorophenyl radicals and the chloromethyl and 3-chloropropyl radicals.

Preferred radicals R are alkyl and cycloalkyl radicals having 1 to 10 carbon atoms, the methyl, ethyl, isopropyl, tert-butyl, cyclopentyl and cyclohexyl radicals being particularly preferred.

X is preferably fluorine, chlorine or bromine, chlorine being particularly preferred.

The tetravalency of the silicon atom is applicable in all formulae.

The 1,3-dihalo-1,1,3,3-tetra(organyl)disiloxanes of the general formula (1) which are prepared by the process according to the invention as well as the 1,3-dihydro-1,1,3, 3-tetra(organyl)disiloxanes of the general formula (2) which are used as starting materials according to the invention are organosilicon compounds which are liquid or solid at room temperature and 1013 hPa.

Preferred examples of the disiloxanes of the general formula (1) which are prepared by the process according to the invention are
1,3-dichloro-1,1,3,3-tetramethyldisiloxane,
1,3-dichloro-1,1,3,3-tetraethyldisiloxane,
1,3-dichloro-1,1,3,3-tetra-n-propyldisiloxane,
1,3-dichloro-1,1,3,3-tetraisopropyldisiloxane,
1,3-dichloro-1,1,3,3-tetra-n-butyldisiloxane,
1,3-dichloro-1,1,3,3-tetraisobutyldisiloxane,
1,3-dichloro-1,1,3,3-tetra-sec-butyldisiloxane,
1,3-dichloro-1,1,3,3-tetra-tert-butyldisiloxane,
1,3-dichloro-1,1,3,3-tetracyclopentyldisiloxane,
1,3-dichloro-1,1,3,3-tetracyclohexyldisiloxane,
1,3-dichloro-1,3-diethyl-1,3dimethyldisiloxane,
1,3-dichloro-1,3-dimethyl-1,3-di-n-propyldisiloxane,
1,3-dichloro-1,3-dimethyl-1,3-diisopropyldisiloxane,
1,3-dichloro-1,3-di-n-butyl-1,3-dimethyldisiloxane,
1,3-dichloro-1,3-diisobuty-1,3-dimethyldisiloxane,
1,3-dichloro-1,3-di-sec-butyl-1,3-dirnethyldisiloxane,
1,3-dichloro-1,3-di-tert-butyl-1,3-dimethyldisiloxane,
1,3-dichloro-1,3-dicyclopentyl-1,3-dimethyldisiloxane,
1,3-dichloro-1,3-dicyclohexyl-1,3-dimethyldisiloxane,
1,3-dichloro-1,3-diethyl-1,3-di-n-propyldisiloxane,
1,3-dichloro-1,3-diethyl-1,3-diisopropyldisiloxane,
1,3-dichloro-1,3-di-n-butyl-1,3-diethyldisiloxane,
1,3-dichloro-1,3-diisobutyl-1,3-diethyldisiloxane,
1,3-dichloro-1,3-di-sec-butyl-1,3-diethyldisiloxane,
1,3-dichloro-1,3-di-tert-butyl-1,3-diethyldisiloxane, 1,3-dichloro-1,3-dicyclopentyl-1,3-diethyldisiloxane, and
1,3-dichloro-1,3-dicyclohexyl-1,3-diethyldisiloxane.

Preferred dihalotetra(organyl)siloxanes are
1,3-dichloro-1,1,3,3-tetramethyldisiloxane,
1,3-dichloro-1,1,3,3-tetra-isopropyldisiloxane,
1,3-dichloro-1,1,3,3-tetra-n-butyldisiloxane,
1,3-dichloro-1,1,3,3-tetra-sec-butyldisiloxane,
1,3-dichloro-1,1,3,3-tetra-tert-butyldisiloxane,
1,3-dichloro-1,1,3,3-tetracyclohexyldisiloxane,
1,3-dichloro-1,3-dimethyl-1,3-diisopropyldisiloxane,
1,3-dichloro-1,3-di-n-butyl-1,3-dimethyldisiloxane,
1,3-dichloro-1,3-di-sec-butyl-1,3-dimethyldisiloxane,
1,3-dichloro-1,3-di-tert-butyl-1,3-dimethyldisiloxane, and
1,3-dichloro-1,3-dicyclohexyl-1,3-dimethylsiloxane.

The disiloxanes of the general fornula (2) used in the process according to the invention are preferably
1,3-dihydro-1,1,3,3-tetramethyldisiloxane,
1,3-dihydro-1,1,3,3-tetraethyldisiloxane,
1,3-dihydro-1,1,3,3-tetra-n-propyldisiloxane,
1,3-dihydro-1,1,3,3-tetraisopropyldisiloxane,
1,3-dihydro-1,1,3,3-tetra-n-butyldisiloxane,
1,3-dihydro-1,1,3,3-tetraisobutyldisiloxane,
1,3-dihydro-1,1,3,3-tetra-sec-butyldisiloxane,
1,3-dihydro-1,1,3,3-tetra-tert-butyldisiloxane,
1,3-dihydro-1,1,3,3-tetracyclopentyldisiloxane,
1,3-dihydro-1,1,3,3-tetracyclohexyldisiloxane,
1,3-dihydro-1,3-diethyl-1,3-dimethyldisiloxane,
1,3-dihydro-1,3-dimethyl-1,3-di-n-propyldisiloxane,
1,3-dihydro-1,3-dimethyl-1,3-diisopropyldisiloxane,
1,3-dihydro-1,3-di-n-butyl-1,3-dimethyldisiloxane,
1,3-dihydro-1,3-diisobutyl-1,3-dimethyldisiloxane,
1,3-dihydro-1,3-di-sec-butyl-1,3-dimethyldisiloxane,
1,3-dihydro-1,3-di-tert-butyl-1,3-dimethyldisiloxane,
1,3-dihydro-1,3-dicyclopentyl-1,3-dimethyldisiloxane,
1,3-dihydro-1,3-dicyclohexyl-1,3-dimethyldisiloxane,
1,3-dihydro-1,3-diethyl-1,3-di-n-propyldisiloxane,
1,3-dihydro-1,3-diethyl-1,3-diisopropyldisiloxane,
1,3-dihydro-1,3-di-n-butyl-1,3-diethyldisiloxane,
1,3-dihydro-1,3-diisobutyl-1,3-diethyldisiloxane,
1,3-dihydro-1,3-di-sec-butyl-1,3-diethyldisiloxane,
1,3-dihydro-1,3-di-tert-butyl-1,3-diethyldisiloxane,
1,3-dihydro-1,3-dicyclopentyl-1,3-diethyldisiloxane, and
1,3-dihydro-1,3-dicyclohexyl-1,3-diethyldisiloxane.

Preferred dihydrotetra(organyl)siloxanes are
1,3-dihydro-1,1,3,3-tetramethyldisiloxane,
1,3-dihydro-1,1,3,3-tetraisopropyldisiloxane,
1,3-dihydro-1,1,3,3-tetra-n-butyldisiloxane,
1,3-dihydro-1,1,3,3-tetra-sec-butyldisiloxane,
1,3-dihydro-1,1,3,3-tetra-tert-butyldisiloxane,
1,3-dihydro-1,1,3,3-tetracyclohexyldisiloxane,
1,3-dihydro-1,3-dimethyl-1,3-diisopropyldisiloxane,
1,3-dihydro-1,3-di-n-butyl-1,3-dimethyldisiloxane,
1,3-dihydro-1,3-di-sec-butyl-1,3-dimethyldisiloxane,
1,3-dihydro-1,3-di-tert-butyl-1,3-dimethyldisiloxane, and
1,3-dihydro-1,3-dicyclohexyl-1,3-dinethyldisiloxane.

The disiloxanes of the general formula (2) which are used according to the invention are commercial products or can be prepared by processes known in organosilicon chemistry. For example, the dihydrotegra(organyl)siloxanes are obtainable by hydrolysis of halodi(organyl)-H-silanes. Halodi(organyl)-H-silanes are also commercially available products or are obtainable, for example, in the direct synthesis of silicon with haloorganyls (Müller-Rochow process); are obtainable by salt elimination reactions of metal organyls (e.g. Grignard reagents or lithium organyls) with dihalo(organyl)silanes; or trilo-H-silanes and by disproportionation and comproportionation reactions.

The hydrogen halides preferably used in the process according to the invention are hydrogen fluoride, hydrogen chloride and hydrogen bromide, hydrogen chloride being particularly preferred.

The catalysts used in the process according to the invention are transition metals of the 8th subgroup of the periodic table of the elements, and compounds or complexes of these metals. Preferred examples are ruthenium, rhodium, iridimn, palla dium and platinum in powder form, optionally as a mixture with or supported by carbon, active carbon or barium sulfate, and dichlorotetrakis-(triphenylphosphino)ruthenium(II), dichlorotris(triphenylphosphino)ruthenium(I), potassium hexachlororuthenate(IV), potassium $\mu$oxobis[pentachlororuthenate(II)]hydrate, ruthenium(III) acetylacetonate, ruthenium(IV) chloride, ruthenium(III) chloride hydrate, ruthenium(IV) oxide, ruthenium(IV) oxide hydrate, chlorotris(triphenylphosphino)rhodium), potassium hexachlororhodate(III), sodium hexachlororhodate(III), rhodium(III) acetylacetonate, rhodium(IIi) chloride, rhodium(III) chloride hydrate, rhodium(III) oxide, rhodium(III) oxide hydrate, hexachloroiridic(IV) acid hydrate, iridium(III) acetylacetonate, iridium(III) chloride, iridium(III) chloride hydrate, iridium(IV) oxide, iridium(IV) oxide hydrate, potassium hexachloroiridate(III), potassium hexachloroiridate(IV), sodium hexachloroiridate(III) hydrate, sodium hexachloroiridate(IV) hexahydrate, bis(aceto)bis(triphenylphosphino)palladium(II), potassium hexachloropalladate(IV), potassium tetrachloropalladate(II), sodium hexachloropalladate(IV) tetrahydrate, sodium tetrachloropalladate(II), palladium(II) acetate, palladium(II) acetylacetonate, palladium(II) chloride, palladium(II) oxide, palladium(II) oxide hydrate, palladium(II) sulfate, tetrakis(triphenyl-phosphino)palladium(0), hexachloro-platinic(IV) acid hydrate, platinum(II) acetylacetonate, platinum(II) chloride, platinum(IV) chloride, platinum(0)-1,3-divinyl-1,1,3,3-tetramethyldisiloxane, platinum(IV) oxide, potassium hexachloroplatinate(IV), sodium hexachloroplatinate(IV) hexahydrate and tetrakis(triphenylphosphino)platinum(0), and combinations of these compounds.

The catalyst used in the process according to the invention is particularly preferably ruthenium on carbon (e.g. 5% of Ru (by weight)), rhodium on carbon (e.g. 5% of Rh), iridium powder, palladium on active carbon (e.g. 5% of Pd) and platinum on active carbon (e.g. 5% of Pt) and dichloro-tris(triphenylphosphino)ruthenium(II), potassium hexachlororuthenate(IV), ruthenium(III) chloride, ruthenium(IV) oxide, rhodium(III) chloride, hexachloroiridic(IV) acid hydrate, iridium(III) chloride, iridium(IV) oxide, potassium hexachloroiridate(III), potassium hexachloroiridate(IV), bis(aceto)bis(triphenylphosphino)palladium(II), potassium hexachloropalladate(IV), potassium tetrachloropalladate(II), sodium hexachloropalladate(IV) tetrahydrate, sodium tetrachloropalladate(II), palladium(II) chloride, palladium(II) oxide, hexachloroplatinic(IV) acid hydrate, platinum(I) chloride, platinum(IV) chloride, platinum(0)-1,3-divinyl-1,1,3,3-tetramethylsiloxane and platinum(IV) oxide, potassium hexachloroplatinate(IV), in particular palladium on active carbon (e.g. 5% of Pd), platinum on active carbon (e.g. 5% of Pt), palladium(II) chloride, hexachloroplatinic(IV) acid hydrate and platinum(0)-1,3-divinyl-1,1,3,3-tetramethyldisiloxane.

Taking into account a suitable space-time yield but also from economic and ecological points of view, in the process according to the invention the transition metal catalyst is preferably added in an amount of from 0.02 to 100,000 ppm by weight, particularly preferably in an amount of from 1 to 10,000 ppm by weight, calculated as elemental metal, and based on the total amount of disiloxane of the general formula (2) used.

In the process according to the invention, the reaction is preferably carried out at a temperature of from −78° C. to 250° C., more preferably from 0° C. to 150° C. The pressure used in the reaction may be any desired pressure, and depends in particular on the disiloxanes of the formula (2) which are used. Preferably, the reaction of hydrogen halide with the dihydrosiloxanes of the general formula (2) is carried out at a pressure of from 500 hPa to 20,000 hPa, more preferably at the pressure of the surrounding atmosphere, i.e. from 900 to 1100 hPa. The dihydrodisiloxanes are preferably liquid or solid at room temperature and at the chosen pressure. The process is preferably takes place in an inert gas atmosphere in the absence of atmospheric oxygen and moisture. Suitable inert gases are, for example, argon and nitrogen.

If a solid 1,3-dihalo-1,1,3,3-tetra(organyl)disiloxane is formed or if a solid 1,3-dihydro-1,1,3,3-tetra(organyl) disiloxane is used, the reaction is preferably carried out in an organic solvent. If an organic solvent is to be used, it is preferably added in an amount of from 0.01 to 50 equivalents (by weight), more preferably in an amount of from 1 to 5 equivalents (by weight), based in each case on the 1,3-dihydro-1,1,3,3-tetra(organyl)disiloxane used.

Suitable solvents which may be used are aromatic hydrocarbons such as benzene, toluene or xylene; aliphatic hydrocarbons such as n-pentane, n-hexane, n-heptane, n-octane or cyclohexane; and halogenated hydrocarbons. Solvents which reduce the activity of the catalyst or lead to secondary reactions, such as alcohols, tend to be less suitable for the halogenation reaction of to the invention.

In the preparation of liquid 1,3-dihalo-1,1,3,3-tetra (organyl)disiloxanes starting from liquid 1,3-dihydro-1,1,3, 3-tetra(organyl)-disiloxanes, a solvent inert to the components may be used, but is not necessary.

In the process according to the invention, gaseous hydrogen halide is preferably reacted with the disiloxane of the general formula (2) in a molar ratio of from 2:1 to 100:1, more preferably in a ratio of from 2:1 to 40:1,.

After the end of the reaction, the disiloxane of the general formula (1) can be isolated from the reaction mixture by conventional techniques, for example directly by filtration or, for removing a catalyst dissolved in the reaction mixture, with subsequent distillation.

The subject invention process has the advantage that it permits the preparation of dihalodisiloxanes of the general formula (1) in a simple manner and in very good yields. The process has the further advantage that the dihalodisiloxanes are formed with a very high product purity. The hydrogen obtained as the byproduct can be separated easily and quantitatively. Furthermore, the process according to the invention has the advantage that the reaction times are very short and toxicological aspects and safety considerations can be taken into account in the choice of the catalyst.

It is furthermore advantageous that some of the catalysts claimed, for example the metal powders, can be simply separated in pure form, or as a mixture with carbon or active carbon, by known measures such as filtration, decanting or centrifuging of the supernatant liquid, and can be used again as catalysts for further chlorination reactions without detectable loss of activity.

The disiloxanes of the general formula (1) can be used for all purposes for which 1,3-dihalo-1,1,3,3-tetra(organyl) disiloxanes have been used to date. They are used in particular as derivatizing and protective group reagents in organic synthesis for the preparation of pharmaceutical products and agrochemicals, and for analytical purposes.

In the Examples which follow, all parts and percentages are based on weight, unless stated otherwise. Except where indicated to the contrary, the Examples are carried out at the pressure of the surrounding atmosphere, i.e. at about 1000 hPa, and at room temperature, i.e. about 20° C., or at a temperature which is established on combining the reactants at room temperature without additional heating or cooling. Unless stated otherwise, the handling of both the starting materials and the reaction products in the Examples described below is carried out in an inert gas atmosphere comprising argon, in the absence of air and moisture.

EXAMPLE 1

0.3 g ($1.4 \cdot 10^{-4}$ mol Pd) of palladium on active carbon (5% Pd loading) and 61.6 g (0.25 mol) of 1,3-dihydro-1,1,3,3-tetraisopropyldisiloxane (99.1% purity, determined by gas chromatography) are initially introduced into a 250 ml three-necked flask equipped with a stirring rod, ground glass thermometer, jacketed coil condenser and gas inlet tube. Thereafter, this reaction mixture is heated at 45° C. and an amount of about 36.5 g (1.0 mol) of hydrogen chloride gas is passed through over a period of 120 minutes. To separate the catalyst, the suspension is allowed to cool to room temperature and is then filtered. The clear, colorless filtrate contains 1,3-dichloro-1,1,3,3-tetraisopropyldisiloxane in a purity of 99.5% (determined by gas chromatography). The amount of filtrate is 75.5 g (96% yield, based on 1,3-dihydro-1,1,3,3-tetraisopropyldisiloxane).

EXAMPLE 2

The procedure described in Example 1 is repeated with the modification that, instead of 0.3 g of palladium on active carbon (5% Pd), 0.4 g ($1.0 \cdot 10^{-4}$ mol Pt) of platinum on active carbon (5% Pt) is used. The catalyst is likewise separated by filtration after the end of the introduction of hydrogen chloride. The clear, colorless filtrate contains the 1,3-dichloro-1,1,3,3-tetraisopropyldisiloxane in a purity of 99.2% (determined by gas chromatography). The amount of filtrate is 74.9 g (95% yield, based on 1,3-dihydro-1,1,3,3-tetraisopropyldisiloxane).

EXAMPLE 3

The procedure described in Example 1 is repeated with the modification that, instead of 0.3 g of palladium on active carbon (5% Pd), 0.02 g ($1.1 \cdot 10^{-4}$ mol Pd) of palladium(II) chloride is used. The product is isolated by vacuum distillation. At 94–95° C./1 hPa, 70.1 g of 1,3-dichloro-1,1,3,3-tetraisopropyldisiloxane (89% yield, based on 1,3-dihydro-1,1,3,3-tetraisopropyldisiloxane) are obtained.

EXAMPLE 4

The procedure described in Example 1 is repeated with the modification that, instead of 0.3 g of palladium on active carbon (5% Pd), 0.1 g ($2.0 \cdot 10^{-4}$ mol Pt) of hexachloroplatinic(IV) acid hydrate (40% Pt) is used. The product is likewise isolated by vacuum distillation. 71.2 g of 1,3-dichloro-1,1,3,3tetraisopropyldisiloxane (90% yield, based on 1,3-dihydro-1,1,3,3tetraisopropyl-disiloxane) are obtained.

EXAMPLE 5

The procedure described in Example 1 is repeated with the modification that, instead of 0.3 g of palladium on active carbon (5% Pd), 1.0 ml (1.0·10$^{-4}$ mol) of platinum(0)-1,3-divinyl-1,1,3,3-tetramethyldisiloxane complex (0.1 M in polydimethyldisiloxane having a viscosity of 100 mPa·s) is used. The product is isolated by vacuum distillation. 72.0 g of 1,3-dichloro-1,1,3,3-tetraisopropyldisiloxane (91% yield, based on 1,3-dihydro-1,1,3,3-tetraisopropyldisiloxane) are obtained.

EXAMPLE 6

The procedure described in Example 1 is repeated with the modification that, instead of 0.3 g of palladium on active carbon (5% Pd), 0.05 g (1.7·10$^{-4}$ mol) of iridium(III) chloride is used. The product is isolated by vacuum distillation. 71.5 g of 1,3-dichloro-1,1,3,3-tetraisopropyldisiloxane (91% yield, based on 1,3-dihydro-1,1,3,3-tetraisopropyldisiloxane) are obtained. EXAMPLE 7

0.3 g (1.4·10$^{-4}$ mol Pd) of palladium on active carbon (5% Pd) and 33.6 g (0.25 mol) of 1,3-dihydro-1,1,3,3-tetramethyldisiloxane (99.4% purity, determined by gas chromatography) are initially introduced at 30° C. into an apparatus according to Example 1. About 36.5 g (1.0 mol) of hydrogen chloride gas are passed through the reaction mixture over a period of 100 minutes. After the end of the introduction of hydrogen chloride, the catalyst is separated by filtration. The clear, colorless filtrate contains 1,3-dichloro-1,1,3,3-tetramethyldisiloxane in a purity of 99.5% (determined by gas chromatography). The amount of filtrate is 49.1 g (97% yield, based on 1,3-dihydro-1,1,3,3-tetramethyldisiloxane).

EXAMPLE 8

The procedure described in Example 7 is repeated with the modification that, instead of 0.3 g of palladium on active carbon (5% Pd), 0.02 g (1.1·10$^{-4}$ mol) of palladium(II) chloride is used. The product is isolated by distillation. 46.3 g of 1,3-dichloro-1,1,3,3-tetramethyldisiloxane (91% yield, based on 1,3-dihydro-1,1,3,3-tetramethyldisiloxane) are obtained.

EXAMPLE 9

The procedure described in Example 7 is repeated with the modification that, instead of 33.6 g of 1,3-dihydro-1,1,3,3-tetramethyldisiloxane, 47.6 g (0.25 mol) of 1,3-dihydro-1,1,3,3-tetraethyldisiloxane are used. After the end of the introduction of hydrogen chloride, the catalyst is likewise separated off by filtration. The clear, colorless filtrate contains 1,3-dichloro-1,1,3,3tetraethyldisiloxane in a purity of 99.6% (determined by gas chromatography). The amount of filtrate is 63.4 g (98% yield, based on 1,3-dihydro-1,1,3, 3tetraethyldisiloxane).

EXAMPLE 10

The procedure described in Example 7 is repeated with the modification that, instead of 33.6 g of 1,3-dihydro-1,1,3,3-tetramethyldisiloxane, 54.6 g (0.25 mol) of 1,3-dihydro-1,3-di-tert-butyl-1,3-dimethyldisiloxane are used. After the end of the introduction of hydrogen chloride, the catalyst is likewise separated off by filtration. The clear, colorless filtrate contains 1,3-dichloro-1,3-di-tert-butyl-1,3-dimethyldisiloxane in a purity of 99.1% (determined by gas chromatography). The amount of filtrate is 69.9 g (97% yield, based on 1,3-dihydro-1,3-di-tert-butyldimethyldisiloxane).

What is claimed is:

1. A process for the preparation of 1,3-dihalo-1,1,3,3-tetra (organyl)disiloxanes of the general formula

$$XR_2Si—O—SiR_2X \quad (1)$$

by reacting hydrogen halide with the 1,3-dihydro-1,1,3,3-tetra(organyl)disiloxanes of the general formula

$$HR_2Si—O—SiR_2H \quad (2),$$

in which

R are identical or different $C_{1-20}$ hydrocarbon radicals optionally substituted by fluorine or chlorine atoms, and X are identical or different and are each a halogen atom, in the presence of at least one catalyst selected from the group consisting of transition metals of the 8th subgroup of the periodic table of the elements, compounds of transition metals of said 8th subgroup, complexes of transition metals of said 8th subgroup, and mixtures thereof.

2. The process of claim 1, wherein X is chlorine.

3. The process of claim 1, wherein the 1,3-dihydro-1,1,3,3-tetra(organyl)disiloxanes of the general formula (2) which are used are organosilicon compounds which are liquid or solid at room temperature and 1013 hPa.

4. The process of claim 2, wherein the 1,3-dihydro-1,1,3,3-tetra(organyl)disiloxanes of the general formula (2) which are used are organosilicon compounds which are liquid or solid at room temperature and 1013 hPa.

5. The process as claimed in claim 1, wherein the hydrogen halide used is hydrogen chloride.

6. The process as claimed in claim 2, wherein the hydrogen halide used is hydrogen chloride.

7. The process as claimed in claim 3, wherein the hydrogen halide used is hydrogen chloride.

8. The process as claimed in claim 4, wherein the hydrogen halide used is hydrogen chloride.

9. The process as claimed in claim 1, wherein the transition metal catalyst is added in an amount of from 0.02 to 100,000 ppm by weight, calculated as elemental metal of the 8th subgroup and based on the total amount of disiloxane of the general formula (2) used.

10. The process as claimed in claim 2, wherein the transition metal catalyst is added in an amount of from 0.02 to 100,000 ppm by weight, calculated as elemental metal of the 8th subgroup and based on the total amount of disiloxane of the general formula (2) used.

11. The process as claimed in claim 3, wherein the transition metal catalyst is added in an amount of from 0.02 to 100,000 ppm by weight, calculated as elemental metal of the 8th subgroup and based on the total amount of disiloxane of the general formula (2) used.

12. The process as claimed in claim 5, wherein the transition metal catalyst is added in an amount of from 0.02 to 100,000 ppm by weight, calculated as elemental metal of the 8th subgroup and based on the total amount of disiloxane of the general formula (2) used.

13. The process as claimed in claim 1, wherein hydrogen halide is reacted with the disiloxane of the general formula (2) in a molar ratio of from 2:1 to 100:1.

14. The process as claimed in claim 9, wherein hydrogen halide is reacted with the disiloxane of the general formula (2) in a molar ratio of from 2:1 to 100:1.

15. The process as claimed in claim 1, wherein the catalyst used comprises one or more of palladium on active carbon, platinum on active carbon, palladium(II) chloride, hexachloroplatinic(IV) acid hydrate, and platinum (0)-1,3-divinyl-1,1,3,3-tetramethyldisiloxane.

16. The process as claimed in claim 2, wherein the catalyst used comprises one or more of palladium on active carbon, platinum on active carbon, palladium(II) chloride, hexachloroplatinic(IV) acid hydrate, and platinum (0)-1,3-divinyl-1,1,3,3-tetramethyldisiloxane.

17. The process as claimed in claim 3, wherein the catalyst used comprises one or more of palladium on active carbon, platinum on active carbon, palladium(II) chloride, hexachloroplatinic(IV) acid hydrate, and platinum (0)-1,3-divinyl-1,1,3,3-tetramethyldisiloxane.

18. The process as claimed in claim 5, wherein the catalyst used comprises one or more of palladium on active carbon, platinum on active carbon, palladium(II) chloride, hexachloroplatinic(IV) acid hydrate, and platinum (0)-1,3divinyl-1,1,3,3-tetramethyldisiloxane.

19. The process as claimed in claim 9, wherein the catalyst used comprises one or more of palladium on active carbon, platinum on active carbon, palladium(II) chloride, hexachloroplatinic(IV) acid hydrate, and platinum (0)-1,3divinyl-1,1,3,3-tetramethyldisiloxane.

20. The process as claimed in claim 10, wherein the catalyst used comprises one or more of palladium on active carbon, platinum on active carbon, palladium(II) chloride, hexachloroplatinic(IV) acid hydrate, and platinum (0)-1,3-divinyl-1,1,3,3-tetramethyldisiloxane.

* * * * *

UNITED STATES PATENT AND TRADEMARK OFFICE
CERTIFICATE OF CORRECTION

PATENT NO. : 6,284,907 B1
DATED : September 4, 2001
INVENTOR(S) : Jörn Winterfeld et al.

It is certified that error appears in the above-identified patent and that said Letters Patent is hereby corrected as shown below:

Column 8,
Line 62, delete "9" and insert -- 2 --.

Signed and Sealed this

Fifteenth Day of July, 2003

JAMES E. ROGAN
*Director of the United States Patent and Trademark Office*